United States Patent [19]
Bryant

[11] Patent Number: 6,156,566
[45] Date of Patent: Dec. 5, 2000

[54] IN VITRO FERTILIZATION PROCEDURE DISH

[76] Inventor: Debra L. Bryant, 120 Chestnut Ridge Rd., Charlottesville, Va. 22901

[21] Appl. No.: 09/173,649

[22] Filed: Oct. 16, 1998

Related U.S. Application Data

[60] Provisional application No. 60/062,513, Oct. 17, 1997.

[51] Int. Cl.[7] ............................ C12M 1/22; C12N 5/08
[52] U.S. Cl. .............................. 435/305.3; 435/305.2; 435/2; 435/373
[58] Field of Search ........................ 435/325, 347, 435/2, 366, 373, 288.3, 288.4, 305.1–305.4; 359/398; 356/246; 422/102

[56] References Cited

U.S. PATENT DOCUMENTS

| | | |
|---|---|---|
| Re. 35,589 | 8/1997 | Fisch . |
| 3,902,972 | 9/1975 | Beckford ................................ 195/139 |
| 4,012,288 | 3/1977 | Lyman et al. ........................... 195/139 |
| 4,255,522 | 3/1981 | Fusenig et al. . |
| 4,387,972 | 6/1983 | Valencia . |
| 4,589,743 | 5/1986 | Clegg . |
| 4,668,633 | 5/1987 | Walton . |
| 4,725,579 | 2/1988 | Jones ........................................ 514/12 |
| 4,986,965 | 1/1991 | Ushikubo . |
| 5,484,731 | 1/1996 | Stevens ................................ 435/305.3 |
| 5,508,164 | 4/1996 | Kausch et al. .............................. 435/6 |
| 5,512,476 | 4/1996 | Gordon ............................. 435/240.26 |
| 5,627,066 | 5/1997 | Gordon ...................................... 435/2 |

FOREIGN PATENT DOCUMENTS

91/06624  5/1991  WIPO .

*Primary Examiner*—William H. Beisner
*Attorney, Agent, or Firm*—Sheldon H. Parker

[57] ABSTRACT

A culture dish for use in in vitro cell manipulation has an outer rim encompassing, and at right angles to, the periphery of the working surface. A parallel inner wall, spaced from the outer rim, forms a trough along the periphery of the dish. Preferably the outer rim is higher than the inner wall to permit liquid contents to flow into, and be retained within, the trough. Cell indices are etched into the working surface to identify the cell location. Although the dish can be solid or translucent, in most applications the working surface is transparent. The cell indicators can optionally be etched into the bottom side of the working surface to maintain a smooth top surface. A working circle, with a periphery smaller than the inner wall, is inset into the surface of the working surface. Alternatively, the circle can be etched into either the top or bottom side of the surface. A lid can be used in conjunction with the culture dish for storage purposes.

18 Claims, 2 Drawing Sheets

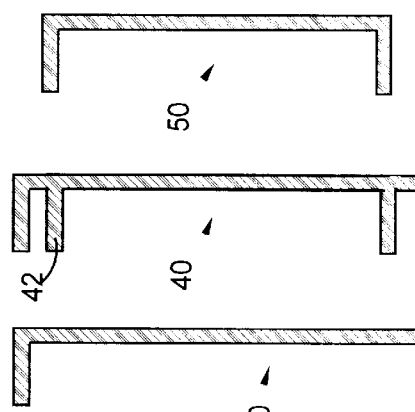
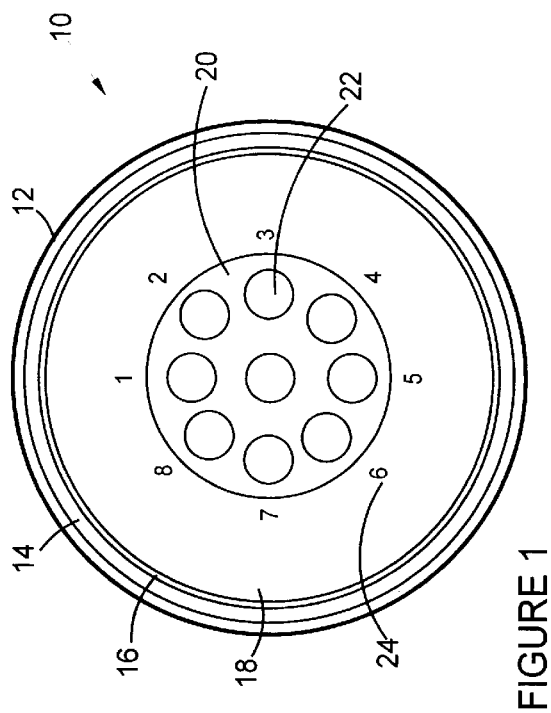
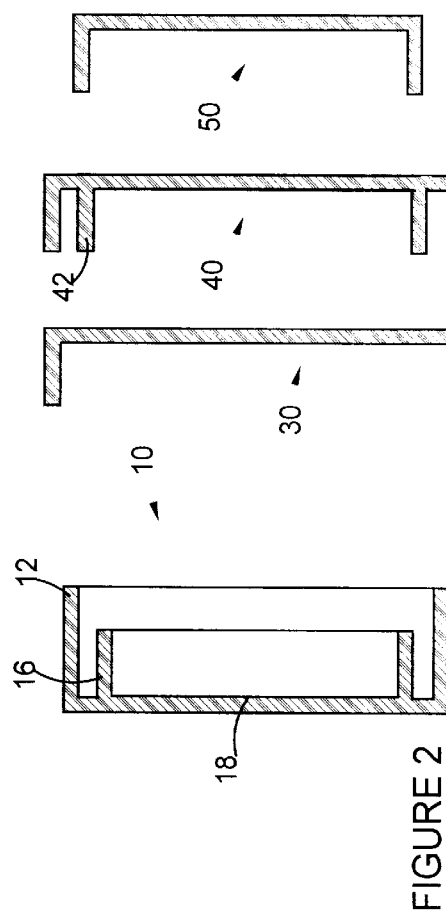

IN VITRO FERTILIZATION PROCEDURE DISH

CROSS-REFERENCE TO RELATED PATENT APPLICATION

The present application claims the benefits under 35 U.S.C. 119(e) of provisional patent application serial No. 60/062,513 filed Oct. 17, 1997.

BACKGROUND OF THE INVENTION

1. Field of the Invention

A tissue culture dish is disclosed the is designed for easy manipulation of cells, specifically intracytoplasmic sperm injection.

2. Brief Description of the Prior Art

Formation and growth of mammalian embryos has become increasing important. The advances in understanding of the mechanisms of ovum generation coupled with advances in ultrasound imaging and micro surgical techniques have fostered a tremendous increase in formation and growth of mammalian embryos, both for domestic animals and especially for human embryos as in vitro fertilization (IVF) techniques have been perfected.

In a human IVF procedure generally the female is treated with hormones to stimulate maturation of multiple ova. These ova are then surgically recovered by micro surgical techniques directly from the ovary. The recovered ova are then placed into a suitable vessel and exposed to sperm collected from the male for fertilization. After fertilization occurs, the fertilized ovum is allowed to grow to a multicelled embryo, then recovered and returned to the female, where implantation of the embryo on the wall of the uterus is expected to occur, resulting, from that time forward, in a normal pregnancy.

In order to generate a suitable embryo for implantation by the IVF procedure briefly outlined above, practitioners must be highly skilled in many manipulative procedures as well as interpretation of laboratory results. Initially, a determination needs to be made of the dosage of hormones to be administered to the female. This determination may involve specialized blood tests, ultrasound imaging and laparoscopic procedures. During the hormone dosage phase, blood hormone levels are determined and ultrasound evaluation of the ovaries is often practiced. The collection of the ova is another specialized procedure involving ultrasound imaging and microsurgery. Once the ova are collected, careful microscale manipulations and optical microscopic evaluation of individual ovum, sperm, fertilized ovum and embryo are part of the process to generate an embryo suitable for ultrasound imaging and micro surgical techniques. In each phase, specialized equipment plays an important role in the success of the procedure.

Specialized equipment has been developed to assist practitioners in every phase of the IVF process. An important part of the process is the phase where the collected ova are placed into a laboratory vessel for the fertilization and growth. Initially, practitioners used ordinary glass petri dishes (hence the "in vitro" [glass] terminology). Specialized laboratory ware such as that disclosed in international Patent Application No. WO 91/06624 by Lyman et al. is available. Lyman et al. teaches a dish for IVF procedures. The dish has a single fertilization well concentrically surrounded by a second well for containing a humidification fluid. The humidification well with the fluid helps to maintain humidity in the fertilization well when the lid, similar to an ordinary petri dish lid, is in place on the dish.

European Publication No. 0 239 450 by Cassou teaches a carousel apparatus for IVF. The Cassou apparatus is complex, holding many dishes and including a glove box for facilitating the handling of the dishes and a microscope for observing the contents of the dishes during manipulation.

There are also multiwell dishes intended for tissue culture. U.S. Pat. No. 3,883,398 to Ono teaches a multiwell microculture slide chamber for simultaneous growing of a plurality of monolayer cell cultures on a slide which can then be separated for microscopic study of the culture.

U.S. Pat. No. 5,484,731 to Stevens discloses a Multiwell In-Vitro Fertilization Plate for receiving ova, forming, evaluating, holding, manipulating and culturing embryos. The well containing body of the device is provided with lids which close over the wells and allow for incubation.

The use of the wells, some of which are relatively deep, restrict operator and/or equipment movement.

The disclosed procedure dish eliminates the prior art problems by providing an easy device for moving and manipulating cells.

SUMMARY OF THE INVENTION

A culture dish for use in in vitro cell manipulation is disclosed that has a working surface encompassed by an outer rim a right angle to the periphery of the working surface. An inner wall is parallel to, and spaced from, the outer rim to form a trough along the periphery of the dish. In the preferred embodiment the outer rim height has a height greater than the inner wall. Cell indices are etched into said working surface, generally on the bottom surface, to identify the cell location, although the indices can be marked directly onto the working surface at the time of use. Although the dish can be solid or translucent, in most applications the working surface is transparent. A working circle, with a periphery smaller than the inner wall, is incorporated into the design. The working circle can be recessed into the working surface or etched into either the top or bottom side of the surface.

A lid can be used in conjunction with the culture dish. The lip of the lid can fit on either the inside or the outside of the outer rim or, alternatively, the lid can incorporate an inner leg to form a friction fit on either side of the outer rim.

BRIEF DESCRIPTION OF THE DRAWINGS

The advantages of the instant disclosure will become more apparent when read with the specification and the drawings, wherein:

FIG. 1 is a top view of the procedure dish of the instant invention;

FIG. 2 is a cutaway side view of the procedure dish of the instant invention;

FIG. 3 is a cutaway side view of a lid for the procedure dish of FIG. 1;

FIG. 4 is an alternate lid embodiment with dual legs;

FIG. 5 is an additional embodiment of a lid which fits within the procedure dish trough.

DETAILED DESCRIPTION OF THE INVENTION

Figure 6:
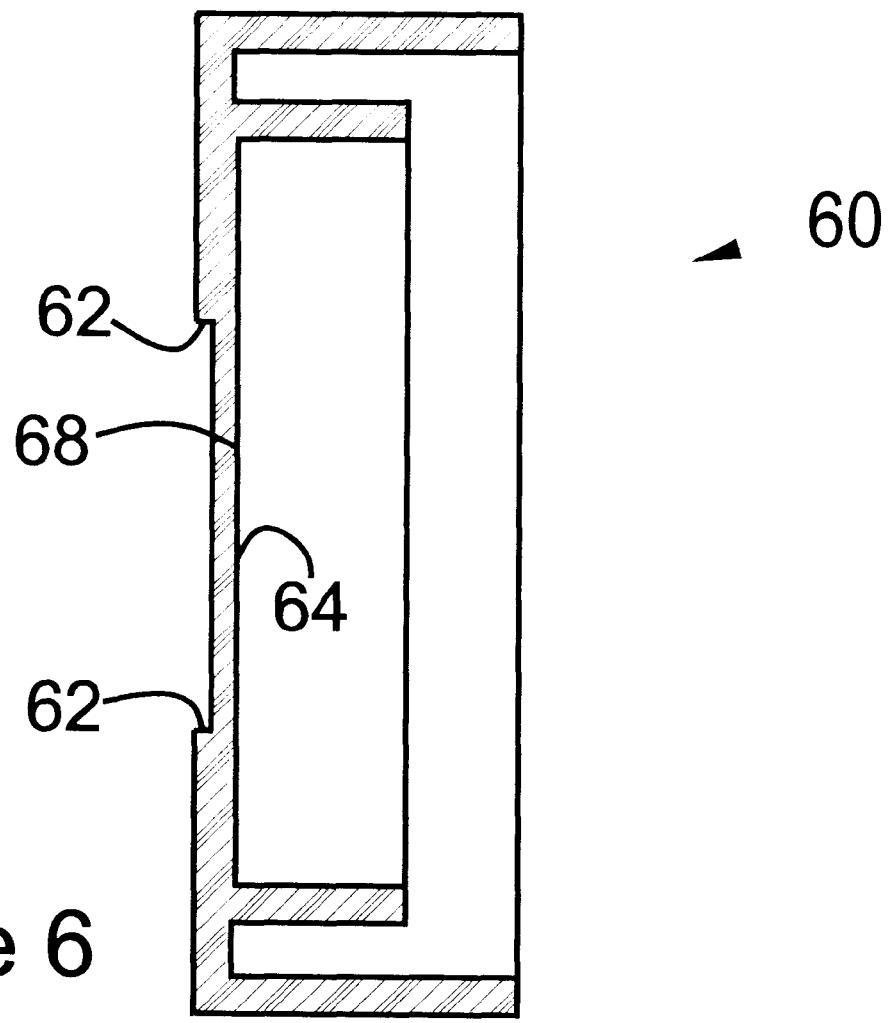
FIG. 6 is a cutaway side view of the dish incorporating an inset working surface.

The manipulation of sperm and oocyte requires equipment that provides high magnification, clear visibility and easy accessibility to the cells. Although various patents have issued to facilitate cell manipulation, they have disclosed the use of micro chambers within which to maintain the sperm and oocyte. Since chambers are not necessarily universally advantageous, many technicians have used glass slips to perform intra cytoplasmic sperm injection. The disadvantage to the slips is the spillage of media and/or oil and the lack of readily available labeling indicators.

The disclosed dish provides a smooth, scratch resistant surface surrounded by dual walls that provide an overflow trough. In use, the sperm and oocyte are placed, in combination with a drop of medium, in the appropriate cell indicator 22 on the dish 10. Mineral oil is placed over the cell/medium combination to eliminate unwanted gas exchange. The procedure dish 10, as illustrated in FIG. 1, is encompassed along the periphery with an outer rim 12 and an interior trough wall 16, thereby forming trough 14. The working surface 18 of the dish 10 is a smooth flat surface with a thickness of about 3 mm. This thickness provides a clear, crisp image in the transparent dishes. It is preferable in most applications, that the procedure dish 10 be manufactured from a plastic, or composite, having predetermined attributes such as a transparent surface, in combination with transparent, opaque or solid walls, that prevents distortion and permits direct light transfer. Alternatively, the viewing surface can be manufactured from a distortion free magnification material. Some applications may not require the transparent working surface and for use in these applications the dish can be opaque or solid. Alternatively the dish 10 can be manufactured from glass, although the breakage factor and cost are both dramatically increased.

As illustrated in FIG. 2, the outer rim 12 has a greater height from the working surface 18 than the interior trough wall 16 forming uneven walls around the trough 14. This permits the trough 14 to provide an overflow receiving area during the fertilization procedure, with the overflow being retained within the trough 14 rather than overflowing the rim 12 onto the microscope stage. The elimination of the trough wall 16 would cause the trough 14 to fill immediately upon the application of the mineral oil, thereby eliminating the retention benefits achieved from the trough 14. Maintaining both the outer rim 12 and the trough wall 16 at the same height would permit for overflow onto the microscope stage without first filling the trough 14. The height of the trough wall 16 must be sufficient to permit the addition of mineral oil to the depth required for the individual application without overflow. The height of the trough wall 16, width of the trough and height of the outer rim 12 will vary dependent upon the final application. When used to hold less a less viscous material, the reduced height of the trough wall would not be as critical and dual walls having the same height would provide some advantage to the use.

The working surface 18 must be smooth to permit easy transfer of the cells from one cell indicator 22 to another. In the illustrated embodiment, cell indicators 22 have been etched into the bottom surface of the dish 10, thereby maintaining a smooth working surface 18 to facilitate cell transfer. In one embodiment, an inner working surface 20 is formed by having a working circle 26 etched into the bottom surface and the cell indicators 22 placed within the inner working surface 20. In another embodiment, as illustrated in FIG. 6, the inner working circle 68 of the dish 60 has a reduced thickness to further reduce distortion and facilitate light transmission. This reduced thickness must be accomplished with the least amount of distortion at the reduction point 62. It is generally preferable that the reduction be on the underside of the working surface to maintain a smooth working surface 64, however in some applications, placing the reduction as a "cup" within the working circle would be useful.

The illustrated dish 10 consists of an outer circle of etched circles with an inner circle placed in the middle of the etched circles. This design is based on fertilization procedures which place the sperm in the center with oocytes in the outer circle, although other designs can be used. Indices 24 are placed adjacent the outer ring of indicators 22, thereby allowing for the identification of each oocyte. The etched bottom indicators may not be desired in some instances and an unmarked bottom manufactured. In some applications, some or all of the etching can be placed on the upper surface of the dish. Since the placement of the etching on the upper surface inhibits movement of the cells, selected placement of the etching on the upper surface permits the user to trap some cells while easily moving others. Etching the working circle on the top surface of the dish will inhibit cell movement toward the periphery.

An example of the approximate dimensions applicable for intra cytoplasmic sperm injection are a working surface 18 having a 4.5 cm diameter and a 2 cm working circle 26. The cell indicators 22 are approximately 4 mm and numbered along the extremity of the working circle 26. The outer rim 12 and inner wall 16 are separated about 1.5 mm with the outer rim 12 having a height of about 4 mm and the inner wall having a height of about 2.5 mm. These dimensions are provided as an example of the ratios that are applicable to this application and will vary dependent upon the final use of the dish.

The procedure dish 10 can be provided with a lid that permits the dish to be used in an incubator. The lid 30 of FIG. 3 is designed to fit over the rim 12, lying flush with the edge of the rim 12. The lid 40 of FIG. 4 has inner legs 42 and outer legs 44 which fit on either side of the rim 12 and can be dimensioned to provide a friction fit between the legs 42 and 44 and the rim 12. The lid 50 of FIG. 5 fits inside the rim 12 within the trough 14. Other lid configurations can be used and will be obvious to those skilled in the art.

Although the disclosure heretofore makes reference to intracytoplasmic sperm injection, it should be noted that the foregoing dish can be used in conjunction with any procedure which requires precise cell manipulation. It should also be noted that the material used in the construction of the procedure dish must meet standard medical criteria as known in the art, including the ability to be sterilized by Gamma Radiation, ethylene oxide or other method applicable to the materials used.

Since other modifications and changes varied to fit particular operating requirements and environments will be apparent to those skilled in the art, the invention is not considered limited to the example chosen for the purposes of disclosure, and covers all changes and modifications which do not constitute departures from the true spirit and scope of this invention.

What is claimed is:

1. A culture dish for use in in vitro cell manipulation, said dish having:

a working surface, said working surface having a first side and a second side and a first predetermined attribute;

an outer rim, said outer rim having a first height and being at a right angle to said first side and encompassing said dish periphery;

an inner wall, said inner wall having a second height and being parallel to, and spaced from, said outer rim, said second height being less than said first height and forming a periphery around said working surface;

a trough, said trough being formed by space between said outer rim and said inner wall;

a working region within said working surface, said working region having a defined periphery less than said working surface periphery, a second predetermined attribute and a substantially smooth first surface and a substantially smooth second surface, wherein said working region indicates a defined area within said working surface.

2. The dish of claim 1 further comprising at least one cell indicator, each of said at least one cell indicator being within said working region providing a defined area for the placement, identification and retrieval of a cell or group of cells.

3. The dish of claim 2 wherein each of said at least one cell indicator is etched into said working region.

4. The dish of claim 2 wherein at least one of said at least one cell indicator is located on said second surface of said working region thereby providing an unobstructed surface on said first surface to enable movement of cells from one cell indicator to another cell indicator.

5. The dish of claim 2 further comprising indices, said indices being adjacent to and identifying each of said at least one cell indicator.

6. The dish of claim 1 wherein one of said predetermined attributes of said working region is transparency.

7. The dish of claim 6 wherein one of said predetermined attributes of said working region is magnification.

8. The dish of claim 1 wherein said working region is etched into said working surface.

9. The dish of claim 1 wherein said working region is etched into said second side of said working surface.

10. The dish of claim 1 wherein said working region is recessed within said working surface second side, thereby reducing the dimension between said working region first surface and said second side.

11. The dish of claim 1 further comprising a lid, said lid being a U-shaped member and interacting with said outer rim to secure said lid to said dish.

12. The dish of claim 11 wherein said lid further comprising an inner leg, said inner leg being adjacent to said trough when said lid is secured to said dish.

13. A culture dish for use in in vitro cell manipulation, said dish having:

a working surface, said working surface having a first side and a second side;

an outer rim, said outer rim having a height and being at right angles to said first side and encompassing said working surface periphery;

an inner wall, said inner wall having a height less than and being parallel to, and spaced from, said outer rim;

a trough, said trough being formed by said outer rim and said inner wall, a working region, said working region being etched into said working surface and having a periphery less than said working surface periphery, at least one cell indicator, each of said at least one cell indicator being etched into said working region, indices, said indices being proximate and identifying each of said at least one cell indicator.

14. The dish of claim 13 wherein said working surface is transparent.

15. The dish of claim 14 wherein at least one of said at least one cell indicator being etched into said second side of said working surface.

16. The dish of claim 13 wherein said working region is etched into said second side of said working surface.

17. A method of manipulating cells in vitro using a culture dish, said dish having a transparent working surface having a first side and a second side, an outer rim having a height and being at right angles to said first side and encompassing said working surface periphery, a working region within said working surface, said working region having a periphery less than said working surface, an inner wall having a height less than and being parallel to, and spaced from, said outer rim, a trough formed by said outer rim and said inner wall, at least one cell indicator within said working region, each of said at least one cell indicator providing a defined area for the placement, identification and retrieval of a cell or group of cells, an indices proximate to and identifying each of said at least one cell indicator comprising the steps of:

a. placing said dish onto a level work area, b. placing a first cell and medium combination onto a first cell indicator, c. noting said indicies and attributes identifying said first cell, d. repeating steps b and c until all cell and medium combinations have been placed on said cell indicators, e. placing a mineral oil covering over said working surface to eliminate gas exchange, f. moving said cells from a first cell indicator to a second cell indicator, g. noting the indicies and attributes for said moved cell, wherein said cells are manipulated within said dish within said medium and said mineral oil, excessive and displaced mineral oil overflowing said inner wall being trapped within said trough and prevented from leaving said dish by said outer rim.

18. The method of claim 17 further comprising the step of covering said dish with a lid, said lid securely covering said dish.

* * * * *